US00RE40185E

(19) United States
(12) Reissued Patent
Kikuchi et al.

(10) Patent Number: US RE40,185 E
(45) Date of Reissued Patent: Mar. 25, 2008

(54) INSERTION SYSTEM FOR INTRAOCULAR LENS

(75) Inventors: Toshikazu Kikuchi, Chiba-ken (JP); Toshiyuki Nakajima, Chiba-ken (JP); Kenichi Kobayashi, Chiba-ken (JP)

(73) Assignee: Canon Staar Co., Inc., Tokyo (JP)

(21) Appl. No.: 10/972,114

(22) Filed: Oct. 22, 2004

Related U.S. Patent Documents

Reissue of:
(64) Patent No.: 6,468,282
Issued: Oct. 22, 2002
Appl. No.: 09/745,123
Filed: Dec. 20, 2000

(51) Int. Cl.
*A61F 9/00* (2006.01)
A61F 11/00

(52) U.S. Cl. ..... 606/107

(58) Field of Classification Search ..... 606/107, 606/108; 623/6.11, 6.12, 5.16
See application file for complete search history.

(56) References Cited

U.S. PATENT DOCUMENTS 4,681,102 A * 7/1987 Bartell ..... 606/1
5,098,439 A * 3/1992 Hill et al. ..... 606/107
5,190,552 A * 3/1993 Kelman ..... 606/107
5,275,604 A * 1/1994 Rheinish et al. ..... 606/107
5,474,562 A * 12/1995 Orchowski et al. ..... 606/107
5,496,328 A * 3/1996 Nakajima et al. ..... 606/107
5,643,275 A * 7/1997 Blake ..... 606/107
5,807,400 A * 9/1998 Chambers et al. ..... 606/107
5,860,984 A * 1/1999 Chambers et al. ..... 606/107
5,873,879 A * 2/1999 Figueroa et al. ..... 606/107
5,947,975 A * 9/1999 Kikuchi et al. ..... 606/107
6,336,932 B1 * 1/2002 Figueroa et al. ..... 606/107

FOREIGN PATENT DOCUMENTS

JP 58-146346 * 8/1983
JP 5-103803 * 4/1993
JP 7-23991 * 1/1995
JP 9-506285 * 6/1997

* cited by examiner

*Primary Examiner*—Pedro Philogene
(74) *Attorney, Agent, or Firm*—Morgan & Finnegan, LLP

(57) ABSTRACT

An insertion system for an intraocular lens includes an intraocular lens having a deformable optical portion, a lens package for storing the lens in a state in which no stress acts on the optical portion of the lens, a deforming member for deforming the lens to a reduced size, and an insertion device. The insertion device has an insertion tube through which the deformed lens is inserted into an eye, and a pusher mechanism for pushing and inserting the lens into the eye. The lens package has a function for attachment to the insertion device and a function for acting as a portion of the mechanism to be provided by the insertion device.

31 Claims, 5 Drawing Sheets

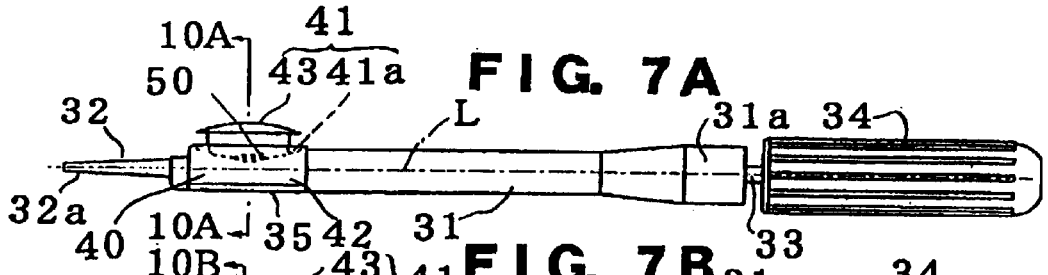
FIG. 7A
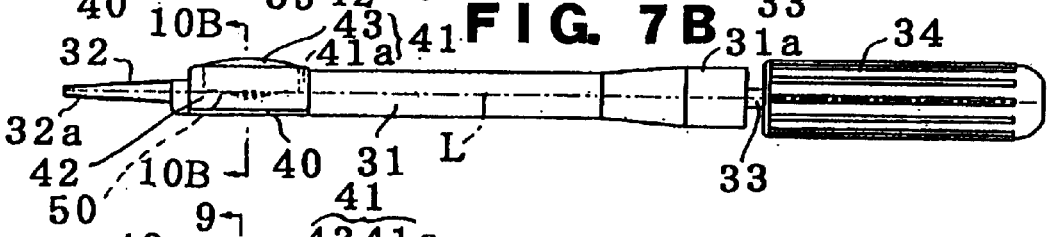
FIG. 7B
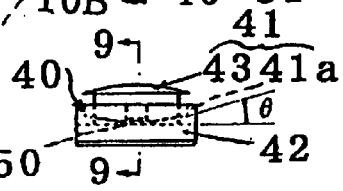
FIG. 8A
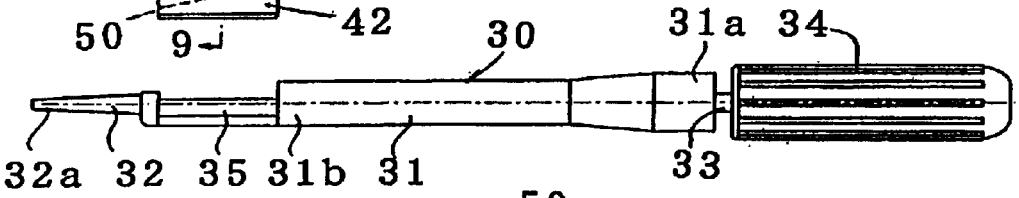
FIG. 8B
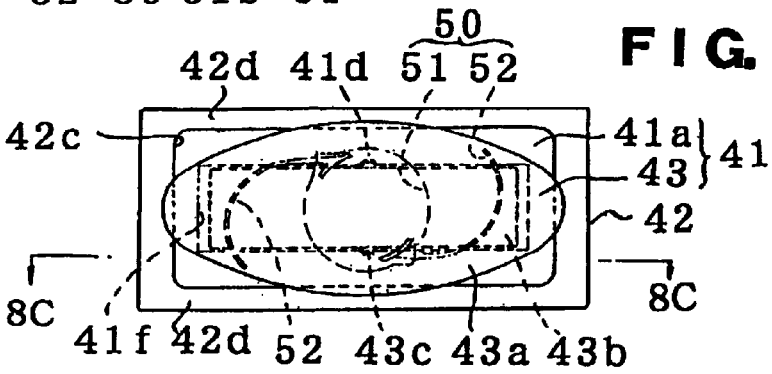
FIG. 8C
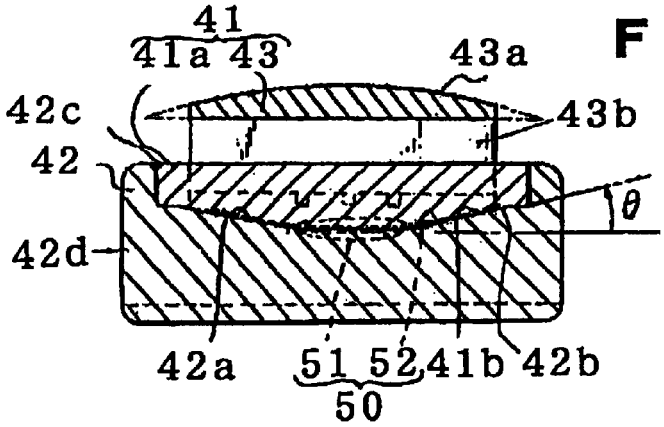

INSERTION SYSTEM FOR INTRAOCULAR LENS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a system for inserting a deformable intraocular lens into the eye. Examples of such a deformable intraocular lens include a deformable intraocular lens that is inserted into the eye in place of the natural lens when the later is physically extracted because of cataracts, and a vision correction lens that is inserted into the eye for the sole purpose of vision correction.

2. Description of the Related Art

In general, during cataract surgery, an intraocular lens is inserted into the eye, from which the natural lens has been removed (lens-removed eye), such that the intraocular lens is located in the original position previously occupied by the natural lens and restores vision. Various studies on the material and shape of such an intraocular lens have been carried out since Ridley performed the first implantation of an artificial lens in 1949.

In recent years, in addition to studies on intraocular lenses which are used for vision restoration after cataract surgery, intense studies on intraocular lenses for refractivity correction have been ongoing. Such an intraocular lens for refractivity correction is inserted into the eye which still has a natural lens (lens-carrying eye), for correction of nearsightedness or farsightedness.

In relation to cataract surgery, a technique for crushing the lens tissue by means of ultrasonic emulsification and suctioning the crushed tissue away has been popularized. This technique enables performance of lens removal surgery to excise an opaque lens through a small incision. Along with progress in the operational technique itself, intraocular lenses themselves have recently been improved. Such an improved intraocular lens is disclosed in, for example, Japanese Patent Application Laid-Open (kokai) No. 58-146346. In the intraocular lens, the optical portion is made of a deformable elastic material. The intraocular lens is inserted, in a folded state, into the eye through a small incision and restored to its original shape within the eye allowing it to exert its proper lens function.

Accompanying these technical developments, the material of the optical portion of such an intraocular lens has been changed gradually from hard polymethyl methacrylate (PMMA) to silicone or soft acrylic resin, which enables the intraocular lens to be inserted into the eye in a folded state.

Moreover, in recent years, studies have been conducted on copolymers such as hydroxyethyl methacrylate and methyl methacrylate, as well as on hydrophilic materials such as 2-hydroxyethyl methacrylate (HEMA).

Further, intraocular lenses of different shapes have been studied and put into practical use, including an intraocular lens having a circular optical portion and loop-shaped support portions formed of different materials, an intraocular lens whose loop-shaped support portions and optical portion are formed of the same material, and an intraocular lens having plate-shaped support portions.

Furthermore, the following patent publications disclose insertion devices for inserting the above-described deformable intraocular lens into the eye in a compressed or folded state.

(1) Japanese Patent Application Laid-Open (kokai) No. 5-103803 discloses a device designed such that a holding member which holds a folded lens is attached to a main body, and the lens is inserted into the eye through an insertion tube provided at the tip end of the holding member.

(2) Japanese Patent Application Laid-Open (kokai) No. 7-23991 discloses a disposable insertion device for one-time use in which a portion for holding a folded lens is integrated with a main body of the device and the entirety of the device is formed of resin.

(3) Japanese Kohyo (PCT) Patent Publication No. 9-506285 discloses an intraocular-lens insertion device having a broadened range of applications. In the intraocular-lens insertion device, a lens is held in a stress-free state in an intermediate preparation region of a main body. After attachment of a cannulae (insertion tube) to the main body, the intraocular lens is inserted into the eye through the cannulae. The intermediate region serves as a lens package.

The conventional intraocular-lens insertion devices described in (1) and (2) above have the following drawbacks. When either of these devices is used, an intraocular lens removed from a package is placed on a placement portion of the device, is deformed, and then inserted into the eye. Therefore, during actual operation, work for placing the intraocular lens onto the device is needed, resulting in increased time and labor involved in implantation of the intraocular lens.

Further, such an intraocular lens and insertion device must be made germ-free through a sterilization procedure, because they are inserted into the eye through an incision. However, if an operator accidentally drops the lens and/or the insertion device onto an unclean surface, such as a floor or table, during the placement operation, the germ-free state is lost, and the lens and/or the insertion device become unusable.

Further, when the operator forcedly inserts into the eye an intraocular lens which has been placed on the device improperly, the lens may be broken, or may forcible fly out from the insertion tube, potentially resulting in damage to the internal tissue of the eye.

The intraocular-lens insertion device described in (3) above has the following drawbacks. Although the intermediate region of the device can be used as a lens package, work for attaching a cannulae (insertion tube) to the main body must be performed during actual use, because the cannulae (insertion tube) is a member which is formed separately from the main body. Although a technique for storing in advance an intraocular lens at the intermediate region located on the center axis of a push rod, the intermediate region is difficult to be formed from a material suitable for storing the lens. In addition, the intermediate region cannot be formed to have a function necessary for properly holding an intraocular lens having loop-shaped support portions. That is, although such an intraocular lens must be stored in a state in which the angle between the optical portion and the support portions of the intraocular lens is maintained, the intermediate region of the conventional insertion device cannot provide such an angle maintaining function.

SUMMARY OF THE INVENTION

An object of the present invention is to provide an insertion system for a deformable intraocular lens, which system eliminates or simplifies an operation of placing a lens on an insertion device to thereby save the time involved in the placement operation, while solving drawbacks involved in conventional insertion devices, such as breakage of a lens or improper insertion of a lens, which would otherwise be caused by an improper operation by an operator.

Another object of the present invention is to provide an insertion system for a deformable intraocular lens, which system enables an operator to freely select an intraocular lens and an insertion device in consideration of a selected operation method or the status of a patient.

In order to achieve the above objects, the present invention provides an insertion system for an intraocular lens, comprising: an intraocular lens having a deformable optical portion; a lens package for storing the lens in a state in which no stress acts on the optical portion of the lens; deforming means for deforming the lens to a reduced size; and an insertion device having, an insertion tube through which the deformed lens is inserted into an eye, and a pusher mechanism for pushing and inserting the lens into the eye. The lens package has a function for attachment to the insertion device and a function for acting as a portion of the mechanism to be provided by the insertion device.

The insertion system according to the present invention eliminates or simplifies an operation of removing an intraocular lens from a lens case and setting a lens on an insertion device. In addition, the insertion system according to the present invention prevents erroneous operation, to thereby improve safety. Further, the insertion system enables an operator to freely select an intraocular lens and an insertion device to thereby obtain an intraocular-lens insertion system optimal for a selected operation method or the status of a patient.

Preferably, the deforming means is formed integrally with the insertion tube. In this case, the structure of the insertion device for deforming the intraocular lens can be simplified.

Preferably, at least a portion of the deforming means is formed integrally with the lens package. In this case as well, the structure of the insertion device for deforming the intraocular lens can be simplified.

Preferably, when the lens package is attached to the insertion device, the center of the lens coincides with the center axis of a push rod which constitutes the pusher mechanism. This structure enables the intraocular lens to be automatically positioned at a position for use, through an operation of attaching the lens package in the insertion device.

Preferably, the insertion system further comprises a lens moving mechanism for moving the lens from a standby position at which the center of the lens does not coincide with the center axis of a push rod which constitutes the pusher mechanism to an insertion position at which the center of the lens coincides with the center axis of the push rod. This structure enables the lens package to have an additional function other then the function of storing the lens. An example of such an additional function in maintaining an angle between the support portions and the optical portion of the lens. In addition, through a simple operation of moving the lens, the intraocular-lens insertion system can be brought into a state for use.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which:

FIGS. 2A and 2B are views showing a first embodiment of the intraocular-lens insertion system according to the present invention, wherein FIG. 2A is a front view of an insertion device carrying a lens case, and FIG. 2B is a bottom view of the insertion device;

FIGS. 3A to 3D are views showing the lens case shown in FIG. 2A, wherein FIG. 3A is a plan view of the lens case,. FIG. 3B is a left side view of the lens case, FIG. 3C is a right side view of the lens case, and FIG. 3D is a cross section taken along line 3D—3D is FIG. 3A;

FIGS. 7A and 7B are views showing a second embodiment of the intraocular-lens insertion system according to the present invention, wherein FIG. 7A is a front view of an insertion device showing a state in which the lens case has been attached to the insertion device and in which the introcular lens is located at a first or standby position, and FIG. 7B is a front view of the insertion device showing a state in which the lens is located at a second or insertion position;

FIGS. 8A to 8C are views showing a state in which the lens case is separated from the insertion device shown in FIGS. 7A and 7B, wherein FIG. 8A is a front view of the insertion device, FIG. 8B is an enlarged plane view of the lens case, and FIG. 8C is a cross section taken along line 8C—8C in FIG. 8B;

FIG. 9A and 9B are cross sections of the lens case taken along line 9—9 in FIG. 8A, wherein FIG. 9A shows a state in which the intraocular lens is located at a standby position, and FIG. 9B shows a state in which the press member of the lens is located at a insertion position;

FIGS. 10A and 10B are views showing the second embodiment, wherein FIG. 10A is a cross section taken along line 10A—10A in FIG. 7A, and FIG. 10B is a cross section taken along line 10B—10B in FIG. 7B;

DETAILED DESCRIPTION OF PREFERRED EMBODIMENTS

Embodiments of the present invention will be described with reference to the accompanying drawings.

Figure 1:
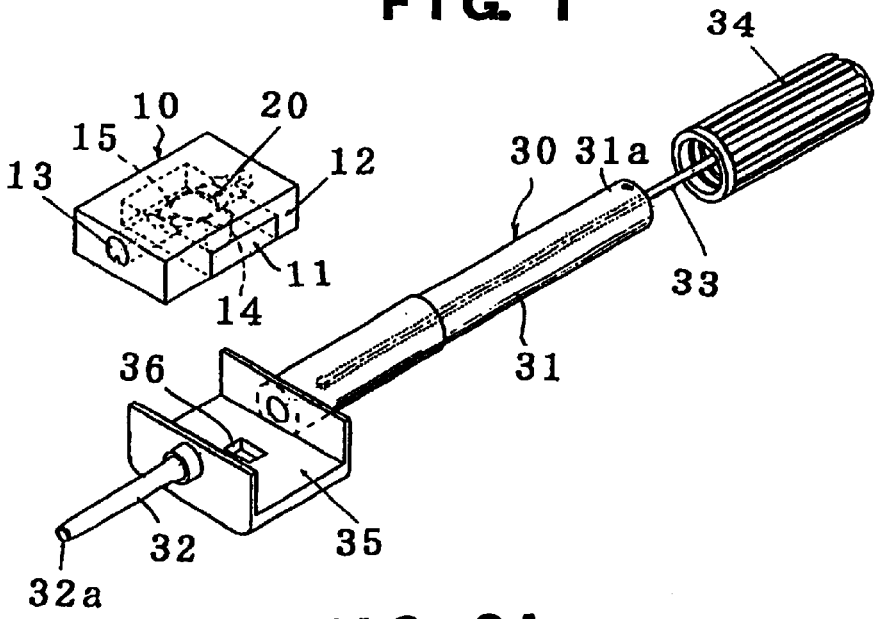
FIG. 1 is a perspective view showing the concept of an intraocular-lens insertion system according to the present invention.

FIG. 1 is a perspective view showing the concept of an intraocular-lens insertion system according to the present invention.

The system according to the present invention is mainly composed of a lens case 10, which serves as a lens package for storing an intraocular lens 20, and an insertion device 30 for inserting the intraocular lens 20 into the eye of a patient.

The lens case 10 includes a lens case top 11 and a lens case bottom 12, which are assembled so as to form a space 15 for storing the intraocular lens 20. The lens case 10 has a through hole 13, which penetrates the lens case 10 in the longitudinal direction thereof and which serves as a portion of the mechanism to be provided by the insertion device 30. An insertion tube 32 is formed at the tip end of the insertion device 30 via an attachment portion 35. The intraocular lens 20 is inserted into the eye of the patient through the insertion tube 32. A pusher mechanism 34 is disposed at the rear end 31a of a tubular main body 31 of the insertion device 30. The pusher mechanism 34 is coupled to the rear end of a push rod 33 for pushing the intraocular lens 20 into the eye.

The lens case 10 is formed to have a size that enables attachment of the lens case 10 to the attachment portion 35 of the insertion device 30. The lens case 10 is fixed onto the attachment portion 35 while being aligned therewith by means of a projection 14 projecting from the lens case top 11 of the lens case 10 and an engagement hole 36 formed in the attachment portion 35. Subsequently, the push rod 33 is advanced by means of the pusher mechanism 34. As a result, the intraocular lens 20 stored in the lens case 10 is pushed out from the tip end 32a of the insertion tube 32 and inserted into the eye.

The above-described structure realizes the concept of the present invention such that when the lens case 10 serving as a lens package is attached to the insertion device 30, the lens case 10 functions as a portion of the mechanism to be provided by the insertion device 30.

Figure 2A:
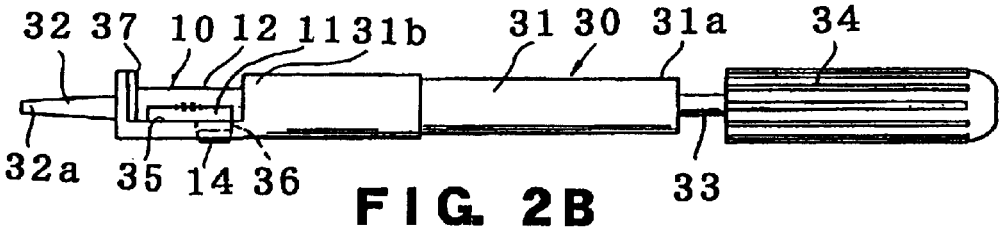
Figure 2B:
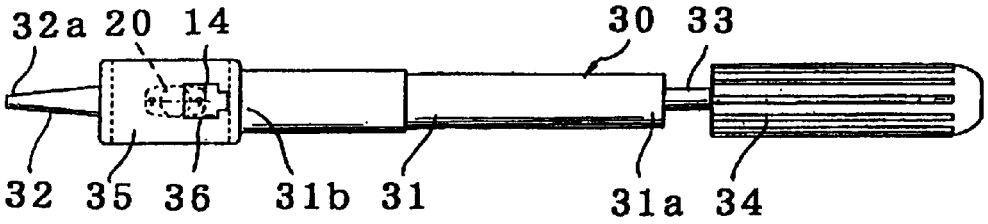

FIGS. 2A and 2B are views showing a first embodiment of the intraocular-lens insertion system according to the present invention, wherein FIG. 2A is a front view of the insertion device 30 to which the lens case 10 has been attached, and FIG. 2B is a bottom view of the insertion device 30.

The tubular main body 31 of the insertion device 30 is formed of transparent or semi-transparent plastic such that the diameter at the base end 31a is smaller than that at the tip end 31b. The above-mentioned push shaft 33 is disposed to be located on the center axis of the tubular main body 31, and the through hole of the tapered insertion tube 32 is aligned with the center axis of the tubular main body 31.

The above-mentioned engagement hole 36 is formed in the horizontal region of the attachment portion 35, and a notch is formed on the rearward-facing surface of a front-side vertical wall of the attachment portion 35. The engagement hole 36 and the notch 37 cooperate to position the lens case 10 relative to the attachment portion 35.

As is clearly shown in FIGS. 3A to 3D, the lens case 10 is constituted through assembly of the lens case top 11, on which is placed the intraocular lens 20, and the lens case bottom 12 formed to cover the upper face of the intraocular lens 20 placed on the lens case top 11.

Figure 3A:
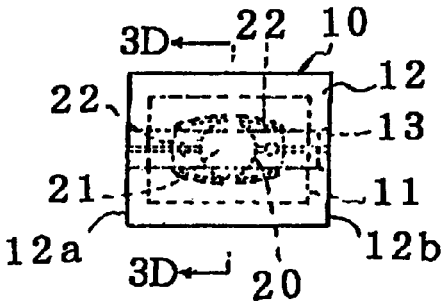
Figure 3B:
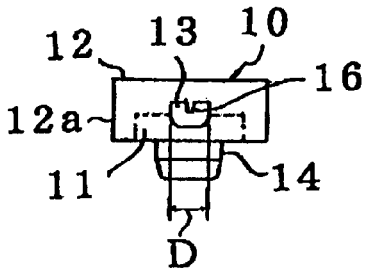
Figure 3C:
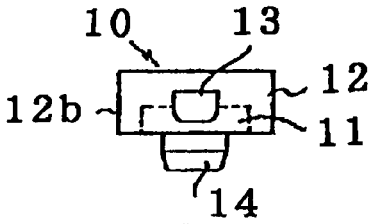
Figure 3D:
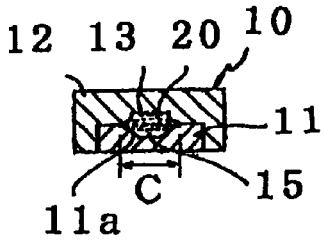

FIG. 3A is a plan view of the lens case, FIG. 3B is a left side view of the lens case, FIG. 3C is a right side view of the lens case, and FIG. 3D is a cross section taken along line 3D—3D is FIG. 3A;

A groove-shaped depression 11a is formed on the upper surface of the lens case top 11 such that the depression 11a extends in the horizontal direction in FIG. 3A. Support portions 22 of the intraocular lens 20 for supporting the optical portion 21 of the intraocular lens 20 are placed in the depression 11a. The above-described projection 14 to be engaged with the engagement hole 36 of the attachment portion 35 is formed on the lower surface of the lens case top 11 to be located at a position which is slightly offset rightward from the center in FIG. 3A. The lens case bottom 12 for covering the upper surface of the lens case top 11 is formed such that the lens case bottom 12 can be fitted onto the lens case top 11 while covering the upper surface and circumferential (side) surface of the lens case top 11. The above-described through hole 13 is formed in the left and right walls 12a and 12b such that the center of the through hole 13 is aligned with the center axis of the tubular main body 31 of the insertion device 30 when the lens case 10 is attached to the attachment portion 35.

The specific procedure for placement of the lens case 10 is as follows. First, the intraocular lens 20 is placed on the lens case top 11 such that the optical portion 21 of the lens 20 corresponds to the depression 11a of the lens case top 11 and such that the optical portion 21 and support portions 22 of the intraocular lens 20 are supported by the edge portions of the depression 11a. Subsequently, the lens case bottom 12 is placed on the lens case top 11, so that a space 15 is formed between the lens case bottom 12 and the lens case top 11. The space 15 has a shape and size such that movement of the intraocular lens within the space 15 is restricted. Further, the shape of the space 15 is determined such that the optical portion 21 of the intraocular lens 20 does not come into contact with the inner surface of the lens case top 11 or the inner surface of the lens case bottom 12, thereby preventing the optical characteristics of the optical portion 21 from changing due to force acting on the optical portion 21 during long-term storage.

The through hole 13 of the lens case 10 is reduced in diameter toward the tip end thereof. The intraocular lens 20 and the push rod 33 pass through the through hole 13. After attachment of the lens case 10 to the insertion device 30, the push rod 33 is advanced through operation of the pusher mechanism 34. As a result, the intraocular lens 20 within the lens case 10 is gradually deformed to a smaller size and is moved into the insertion tube 32. Subsequently, after the tip end 32a of the insertion tube 32 is inserted into the eye through an incision formed thereon, the push rod 33 is advanced further, so that the intraocular lens 20 is deformed to a further reduced size by means of the insertion tube 32 and is then pushed into the eye.

Thus, the lens case 10 provides a portion of the function of the insertion device 30 upon attachment to the insertion device 30.

FIGS. 3B and 3D show the diameter of the through hole 13 of the lens case 10 being gradually reduced toward the tip end thereof. That is, the transverse dimension C of the space 15—which receives the intraocular lens 20 placed on the lens top case 11 of the lens case 10 as shown in FIG. 3D—is reduced to a transverse dimension D which corresponds to that measured at the tip end of the through hole 13 as shown in FIG. 3B. This configuration enables the intraocular lens 20 to enter a deformed state from a non-deformed state while being moved through the through hole 13 by means of the push rod 33.

At the tip end, the through hole 13 has an asymmetrical shape with respect to the vertical direction. Further, rail 16 projecting toward the center of the through hole 13 is formed such that the rail 16 extends in the direction of movement of the intraocular lens 20. This configuration enables the intraocular lens 20 to be formed into an intended shape.

Figure 4:
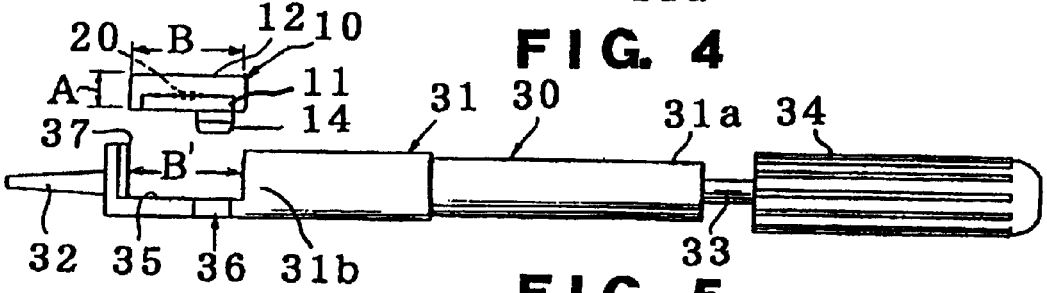
FIG. 4 is a front view corresponding to FIG. 2A and showing a state in which the lens case is separated from the insertion device.

FIG. 4 is a front view showing a state in which the lens case 10 is separated from the insertion device 30 used in the first embodiment of the intraocular-lens insertion system according to the present invention. The notch 37 is formed on a rearward-facing surface of the front-side vertical wall of the attachment portion 35 at a position corresponding to the height A of the lens case 10. The notch function of the notch 37 prevents unintentional separation of the attached lens case 10 from the attachment portion 35. The projection 14 of the lens case 10 and the engagement hole 36 of the attachment portion 35 are formed to have shapes and dimensions which enable establishment of fitting engagement therebetween, so that the relative position between them can be fixed. These mechanism enables the lens case 10 as shown in FIG. 2A to be attached to the insertion device 30.

FIG. 4 shows an example in which the lens case 10 is attached to the insertion device 30 from above. However, the present invention is not limited to such a style of attachment, and an alternative attachment method may be employed. Specifically, the lens case 10 carrying the intraocular lens 20 is placed on a desk or table in a state in which the projection 14 of the lens case top 11 faces upward; and the insertion device 30 is inverted and placed on the lens case 10 from above so as to cover it.

Since such an intraocular-lens insertion system must be used in a germ-free environment, during actual use of the insertion system, an operator must use the system while wearing gloves, which hinders fine operation. Therefore, the above-described attachment method in which attachment of the lens case 10 is achieved through moving the insertion device 30—which is larger and easier to hold than the lens case 10—is preferable.

Figure 5:
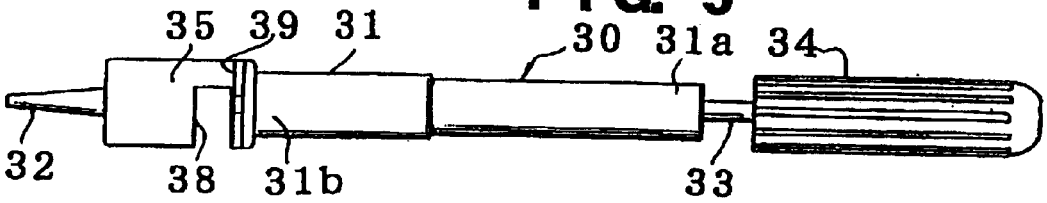
FIG. 5 is a view showing a modification of the first embodiment shown in FIGS. 2A and 2B.
Figure 5:
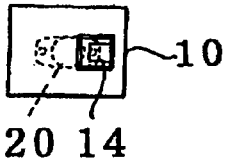

FIG. 5 is a view showing a modification of the first embodiment shown in FIGS. 2A and 2B. In place of the engagement hole 36 provided on the attachment portion 35, an engagement groove 38 is provided. The engagement groove 38 extends in a direction perpendicular to the push rod 33. The lens case 10 is attached to the insertion device 30 from the side thereof and is fixed by means of a notch 39. Portions other than the above-mentioned portions are denoted by the same reference numerals as those used in FIG. 2, and their repeated descriptions are omitted.

In the present embodiment as well, the attachment method employed in the above-described first embodiment can be used. That is, the lens case 10 is placed on a desk or table; and the insertion device 30 is inverted and placed on the lens case 10 from above. This attachment method provides the same effect as that mentioned above.

Figure 6:
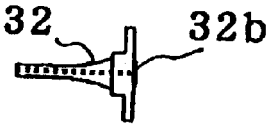
FIG. 6 is a front view showing a modified example of the insertion tube employed in the first embodiment.

FIG. 6 is a front view showing a modified example of the insertion tube 32 employed in the first embodiment.

The insertion tube 32 shown in FIG. 6 is formed to have a tapered through hole whose diameter gradually decreases toward the tip end thereof. Therefore, the intraocular lens 20 pushed into the base end 32b of the insertion tube 32 by means of the push rod 33 can be deformed to a smaller size.

There has been shown an intraocular-lens insertion system designed such that the lens case 10 serving as a lens package provides a portion of the function of the insertion device 30 upon attachment thereto. Further, in the above-described embodiment, the lens case 10 and the insertion tube 32 form deforming means for deforming the intraocular lens 20. However, the present invention is not limited thereto, and the configuration of the system may be modified to assume various configurations; e.g., a configuration such that only the lens case 10 is used to deform the intraocular lens 20 to a small size suitable for insertion into the eye, and the thus-deformed lens 20 is passed through the insertion tube 32 and inserted into the eye; and a configuration such that deforming means is not provided on the lens case 10, but is provided on the insertion tube 32.

In the above-described embodiment, the intraocular lens 20 has plate-shaped support portions 22 extending from the opposite ends of the optical portion 21.

In the specification, the term "center of the intraocular lens 20" refers to the center in the thickness direction located on the optical axis of the optical portion 21.

A second embodiment of the intraocular-lens insertion system according to the present invention will now be described with reference to FIG. 7A to FIG. 13. In the present embodiment, an intraocular lens 50 horizontally stored in a lens case 40 serving as a lens package is moved between a first or standby position at which the vertical position of the center of the intraocular lens 50 does not coincide with the center axis of the push rod 33 of the insertion device 30, and a second or insertion position at which the vertical position of the center of the intraocular lens 50 coincides with the center axis of the push rod 33 of the insertion device 30, so that the intraocular lens 50 can be pushed out by the push rod 33.

FIG. 7A is a front view of the insertion device 30 to which the lens case 40 has been attached and in which the intraocular lens 50 is located at the first or standby position, and FIG. 7B is a front view of the insertion device 30 in which the intraocular lens 50 is located at the second or insertion position.

In the first or standby position shown in FIG. 7A, the vertical position of the center of the lens does not coincide with the center axis of the push rod 33 represented by an alternate long and short dash line L. When a push member 43 of the lens case top 41 is pushed downward in FIG. 7A, the intraocular lens 50 is moved downward to the second or insertion position shown in FIG. 7B, at which the vertical position of the center of the lens substantially coincides with the center axis of the push rod 33. In this second or insertion position, the intraocular lens 50 can be pushed out from the tip end 32a of the insertion tube 32 into the eye through advancing movement of the push rod 33 effected by the pusher mechanism 34 provided at the rear end 31a of the tubular main body 31.

FIGS. 8A to 8C are views showing a state in which the lens case 40 is separated from the insertion device 30. Specifically, FIG. 8A is a front view of the insertion device 30; FIG. 8B is an enlarged plane view of the lens case 40; and FIG. 8C is a cross section taken along line 8C—8C in FIG. 8B.

The attachment portion 35 is attached in advance to the insertion device 30 shown in FIG. 8A. The lens case 40 consists of a lens case top 41 and a lens case base 42 having a structure suitable for supporting the intraocular lens 50 having loop-shaped support portions 52 made of a material different from that of the optical portion 51. Specifically, the lens case base 42 has engagement portions 42b which have inclined surfaces 42a of angle θ extending in opposite longitudinal directions in order to maintain the angle θ between the optical portion 51 and the support portions 52 of the intraocular lens 50. The lens case top 41 has on its bottom surface 41b inclined surfaces to be mated with the inclined surfaces 42a of the lens case base 42. After placement of the lens 50 on the lens case base 42, the lens case top 41 is placed on the lens case base 42, so that the support portions 52 of the lens 50 are sandwiched between the lens case base 42 and the lens case top 41.

Figure 9A:
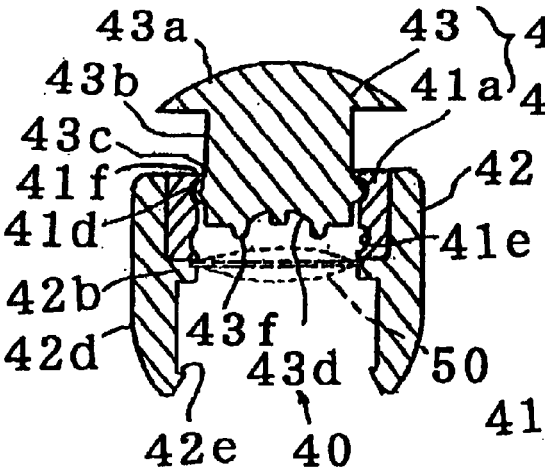
Figure 9B:
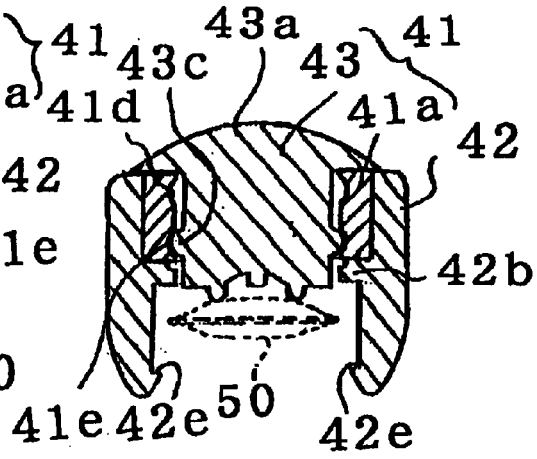

As described above, the lens case top 41 is provided with the push member 43. As shown in FIGS. 9A and 9B, the lens case base 42 has an opening 42c in the top surface thereof and projections 42e in the vicinity of the lower ends of opposite side walls 42d. The projections 42e elastically engage with engagement steps 38 formed in the vicinity of the lower ends of the lateral side surfaces of the attachment portion 35. The longitudinal opposite ends of the lens case base 42 are opened, giving the lens case base 42 a squarish C-like cross section. Further, the paired engagement portions 42b are formed on the inner surfaces of the side walls 42d to be located at the approximate center in the vertical direction. The engagement portions 42b extend in the longitudinal direction and are adapted to receive the peripheral portions of the optical portion 51 and the support portions 52 of the intraocular lens 50. As shown in FIG. 8C, the inclined surfaces 42a each having an inclination angle θ are formed on the engagement portions 42b in order to maintain the angle θ between the optical portion 51 and the support portions 52 of the intraocular lens 50.

The lens case top 41 to be inserted into the top surface opening 42c of the lens case base 42 has a hollow nipping member 41a having a rectangular frame-like shape, and the above-mentioned push member 43 is disposed in the nipping member 41a to be movable in the vertical direction. The bottom surface 41b of the nipping member 41a has inclined portions to come into contact with the inclined surfaces 42a of the engagement portions 42b of the lens case base 42. Upper and lower depressions 41d and 41e are formed at a predetermined interval on each of the inner surface 41c of the opposite lateral walls such that the upper depressions 41d are opposed to each other and the lower depressions 41e are opposed to each other.

The above-mentioned push member 43 is inserted into the opening 41f of the nipping member 41a and is pressed downward in order to move the intraocular lens 50 from the standby position to the insertion position. The push member 43 has a head portion 43a of large diameter and a prism-shaped leg portion 43b. Protrusions 43c are formed on the peripheral surface thereof and in the vicinity of the lower end thereof so as to be engaged selectively with the upper depressions 41d or the lower depressions 41e of the nipping member 41a. Specifically, at the standby position, the protrusions 43c of the push member 43 engage the depressions 41d, and when the push member 43 is pressed, the protrusions 43c move downward and come into engagement with the depressions 41e. A concave surface 43d is formed on the bottom surface of the leg portion 43a, and a ridge 43f for supporting the peripheral portion of the intraocular lens 50 is formed on the concave surface 43d.

Figure 10A:
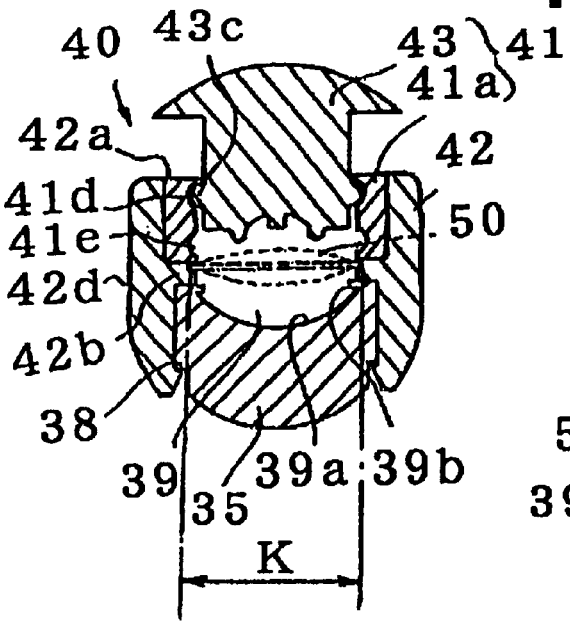
Figure 10B:
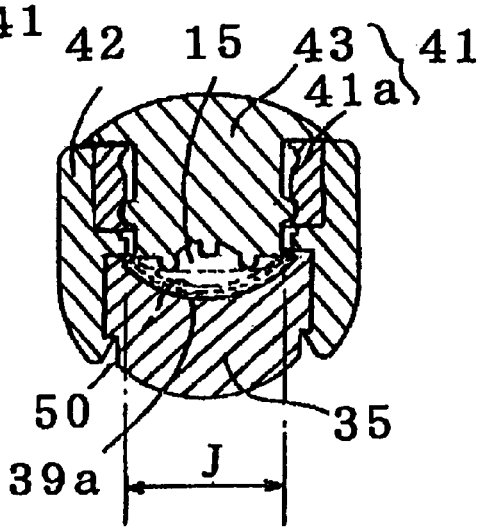

When the intraocular lens 50 is to be moved from the first or standby position shown in FIG. 10A to the second or insertion position shown in FIG. 10B, the head portion 43a of the push member 43 of the lens top 41 is pressed down such that the intraocular lens 50—which is nipped by the lens case base 42 and the lens case top 41 of the lens case 40 is moved to a lens movement portion 39 of the attachment portion 35. The lens movement portion 39 has a shape of a concavely-curved groove. Thus, the peripheral portion of the intraocular lens 50 comes into engagement with the reverse surfaces of the opening projection edges 39b provided at the opening of a curved concave portion 39a. As a result of this movement, the vertical position of the center of the lens 50 substantially coincides with the center axis of the push rod 33. When the push rod 33 is advanced, the intraocular lens 50 is moved within the space 15 of the lens movement portion 39 in the direction perpendicular to the page of FIG. 10B, passed through the insertion tube 32 provided integrally with the attachment portion 35, and then pushed into the eye. Since upon pressing of the push member 43 the protrusions 43c come into engagement with the depressions 41e, the intraocular lens 50 having been moved to the lens movement portion 39 is prevented from reassuming its original shape, and reliable positioning is effected.

The lens case 40 is preferably transparent or semi-transparent, which allows an operator to check whether the lens 50 has been moved to the lens movement portion 39.

Further, it becomes possible to check whether the space 15 for allowing movement of the intraocular lens 50 is formed between the lower surface of the lens case top 41 and the lens movement portion 39 of the attachment portion 35. In other words, the push member 43 of the lens case top 41 provides two functions; i.e., the function for moving the lens 50 downward and the function for forming the lens movement space 15 in cooperation with the attachment portion 35.

As described above, the lens case 40 of the second embodiment—which consists of the lens case base 42 and the lens case top 41 including the nipping member 41a and the push member 43—provides a portion of the mechanism of the insertion device 30 upon attachment thereto.

Further, the present embodiment is characterized in that a portion of deforming means for deforming the intraocular lens 50 to a reduced size is formed integrally with the lens case 40.

That is, when the lens is moved to the lens movement portion 39 of the attachment portion 35, the lens is deformed to a reduced size. This size reduction is achieved by three design features; i.e., the lens movement portion 39 being formed into a form of a curved groove, the lens 50 being moved while been pressed toward the lens movement portion 39 by the lens case top 41, and the dimensional 1 of the lens movement portion 39 being smaller than the dimension K of the lens 50.

Figure 11:
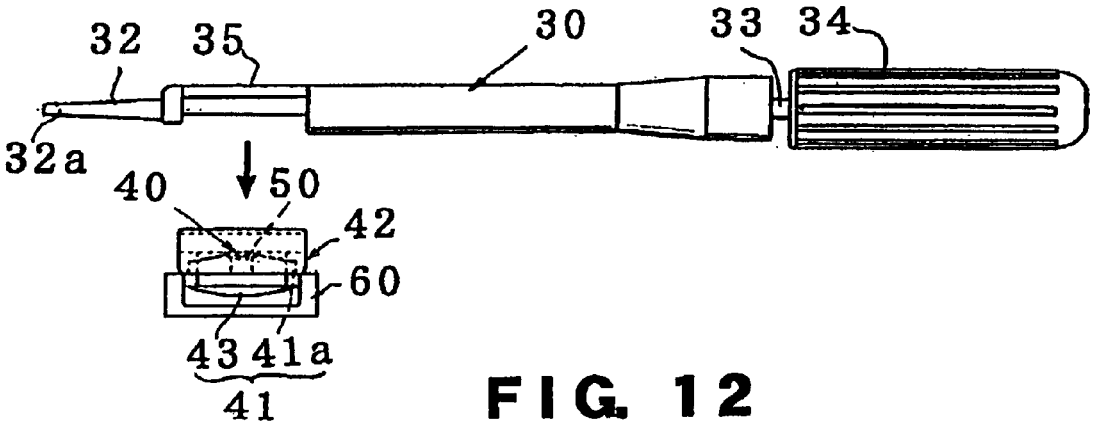
FIG. 11 is a front view of an insertion device showing one modification of the second embodiment shown in FIG. 7A and 7B in a state in which a lens case is separated from the insertion device.

FIG. 11 is a front view of an insertion device showing one modification of the second embodiment shown in FIGS. 7A and 7B in a state in which the lens case 40 is separated from the insertion device 30.

In this modification, the lens case 40 is attached to the insertion device in a manner different from that described with reference to FIGS. 7A and 7B in which the lens case 40 is attached to the attachment portion 35 of the insertion device 30 from above. That is, after the lens case 40 in an inverted state is placed on a lens case support 60, the insertion device 30 is inverted, and the attachment portion 35 of the insertion device 30 is elastically fitted onto the lens case base 42 of the lens case 40. The remaining structure is the same as that of the above-described second embodiment.

During use of the insertion system, an operator wears gloves, which hinders fine operation. Therefore, attachment of the lens case 40 is preferably performed in a method in which an operator places the lens case 40 on a support, holds in his hand the insertion device 30, which is larger and easier to hold than the lens case 40, and fits it onto the lens case 40 from above.

Figure 12:
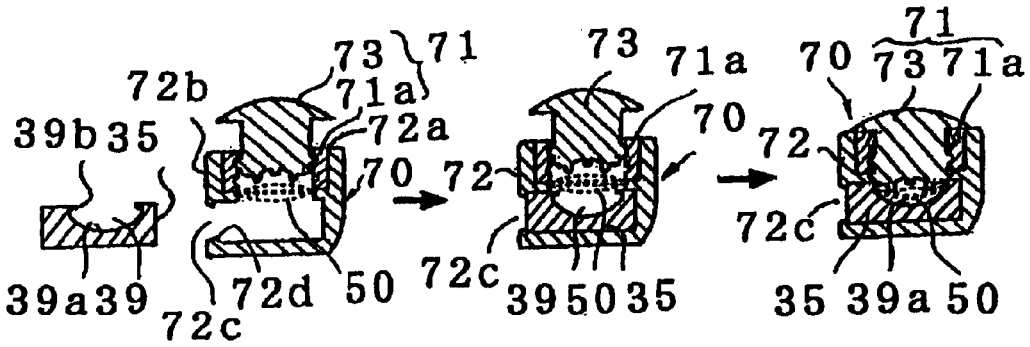
FIG. 12 shows cross section corresponding to those of FIGS. 10A and 10B and showing another modification of the second embodiment shown in FIGS. 7A and 7B, in which the lens case has a modified base portion.

FIG. 12 shows cross sections corresponding to those of FIGS. 10A and 10B and showing another modification of the second embodiment shown in FIGS. 7A and 7B, in which the lens case has a modified base portion.

A lens case base 72 of a lens case 70 according to the present modification has an opening 72a on the top surface, and also has an engagement groove 72c in one of opposite side walls 72b. The engagement groove 72c penetrates the corresponding side wall 72b in a direction perpendicular to the lens insertion direction, and the attachment portion 35 is inserted into the lens case base 72 through the engagement groove 72c. When the lens case base 72 is attached to the attachment portion 35, the relative positioning between the lens case base 72 and the attachment portion 35 is effected by means of a projecting edge 72d formed at the engagement groove 72c and one of the inner surfaces of the side walls 72b.

Further, persons having skill in the art find that the lens case 70 may be easily attached to the insertion device 30 by a different method in which an operator places the lens case 70 on a table, holds in his hand the insertion device 30, and fits the attachment portion 35 into the lens case 70 through the engagement groove 72c.

During use of the invention system, an operator wears gloves, which hinders fine operation. Therefore, attachment of the lens case 70 is preferably performed in a method in which an operator places the lens case 70 on a support, holds in his hand the insertion device 30, which is larger and easier to hold than the lens case 70, and fits it onto the lens case 70 from one side thereof.

The remaining structure is the same as that of the above-described second embodiment. When the intraocular lens 50 is to be inserted into the eye, the push member 73 of the lens case top 71 is depressed to thereby move the introcular lens 50 into the lens movement portion 39 of the attachment portion 35, and the intraocular lens 50 is then inserted into the eye from the tip end of the insertion tube through advancement of the push rod 33.

Figure 13:
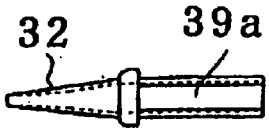
FIG. 13 is a plan view showing a modified example of the insertion tube of the insertion device used in the second embodiment.

FIG. 13 is a plan view showing a modified example of the insertion tube 32 of the insertion device 30 used in the second embodiment.

In this modification, the insertion tube 32 is formed integrally with the attachment portion 35 of the insertion device 30, such that a groove-shaped curved depression 39a serving as a lens deforming means is formed on the base end side of the insertion tube 32.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion system for an intraocular lens comprising:

an intraocular lens having a deformable optical portion;

a lens package for storing the lens in a state in which no stress acts on the optical portion of the lens;

an insertion device having an insertion tube through which the deformed lens is inserted into an eye, the insertion device having a major axis, the insertion device having a means for removably holding the lens package, the means for removably holding being associated with and in communication with the insertion tube, the means for removably holding defining a support which lies parallel to the major axis and an open portion opposite the support, the open portion shaped to receive the lens package; and a pusher mechanism for pushing and inserting the lens into the eye.

2. [An] *The* insertion system for an intraocular lens according to claim 1, further comprising a deforming means, wherein the deforming means is formed integrally with the insertion tube.

3. [An] *The* insertion system for an intraocular lens according to claim 1, further comprising a deforming means, wherein the deforming means is formed integrally with the lens package.

4. [An] *The* insertion system for an intraocular lens according to claim 1, wherein when the lens package is attached to the insertion device, the center of the lens coincides with the center axis of a push rod which constitutes the pusher mechanism.

5. [An] *The* insertion system for an intraocular lens according to claim 1, further comprising a lens moving mechanism for moving the lens from a standby position at which the center of the lens does not coincide with the center axis of a push rod which constitutes the pusher mechanism to an insertion position at which the center of the lens coincides with the center axis of the push rod.

6. An insertion system for an intraocular lens, comprising:

an intraocular lens having a deformable optical portion;

holding means for holding the lens at a standby position in a state in which no stress acts on the optical portion of the lens;

an insertion device having an insertion tube through which the deformed lens is inserted into an eye, and a pusher mechanism for pushing and inserting the lens into the eye, wherein the holding means includes a lens moving mechanism, the lens moving mechanism lockably engaging the holding means in a first position when the lens is held at the standby position, the lens moving mechanism for moving the lens from the standby position to an insertion position at which the pusher mechanism can push and insert the lens into the eye.

7. The insertion system for an intraocular lens according to claim 6, wherein a portion of the deforming means is provided on the lens moving mechanisms.

8. The insertion system for an intraocular lens according to claim 6, wherein the intraocular lens is an intraocular lens having a deformable optical portion and loop-shaped support portions each forming a predetermined angle with respect to the optical portion, and wherein a support-portion holding mechanism for holding the support portions at a predetermined angle is provided.

9. The insertion system for an intraocular lens according to claim 6, wherein the lens moving mechanism and the holding means lockably engage in a second position when the lens is in said insertion position.

10. The insertion system for an intraocular lens according to claim 6, wherein the lens has a center and the pusher mechanism has a center axis, wherein the center of the lens does not coincide with the center axis of the pusher mechanism when the lens is in the standby position.

11. An insertion system for a deformable intraocular lens in a package, the system comprising:

an insertion device having a major axis, the insertion device defining a tubular portion and having a means for removably holding [the] *a* package *for storing the lens in a state in which no stress acts on the optical portion of the lens*, the means for removably holding being associated with and in communication with the tubular portion, the means for removably holding defining a support which lies parallel to the major axis and an open portion opposite the support, the open portion shaped to receive the package; and a pushing mechanism for movement within the tubular portion and the means for removably holding, the pushing mechanism acting to deform the lens and push the lens without the package out of the insertion system.

12. The insertion system of claim 11 wherein the package holds the lens in a non-deformed state.

13. The insertion system of claim 11 wherein the means for removably holding has a means for connecting to the package and receives the deformable intraocular lens in a non-deformed position.

14. The insertion system of claim 11 wherein the package defines an opening for release of the deformable intraocular lens.

15. The insertion system of claim 11 wherein the means for removably holding has two sides connected to the support, the two sides being situated opposite of each other and each having a major surface, one of the two sides having its major surface abutting and communicating with the tubular portion.

16. The insertion system of claim 11 wherein the deformable intraocular lens has an optical portion and support portions connected to the optical portion, the package having an inner surface and an outer surface, wherein the package interacts with the support portions so that the optical portion remains free from contact with the inner surface.

17. The insertion system of claim 11 wherein the package is a quadrilateral shape.

18. An insertion system for a deformable intraocular lens, the system comprising:

an insertion device defining a tubular portion and having means for removably holding the deformable intraocular lens, the means for removably holding being associated with the tubular portion;

a lens moving means lockably engageable with the means for removably holding, the lens moving means movable from a first position to a second position wherein the lens is held in a deformed position in the second position and in a non-deformed state in the first position; and a pushing mechanism for movement within the tubular portion to push the lens out of the system.

19. The insertion system of claim 18 wherein the deformable intraocular lens has an optical portion and support portions connected to the optical portion, the means for removably holding having an inner surface and an outer surface, wherein the means for removably holding interacts with the support portions so that the optical portion remains free from contact with the inner surface of the removably holding means.

20. The insertion system of claim 18 wherein the pushing mechanism comprises a push rod having a center axis, and the lens has a center, wherein the center of the lens does not coincide with the center axis of the push rod when the lens is in the standby position.

21. The intraocular lens insertion system of claim 18, wherein the lens moving means comprises a push member, the push member having protrusions formed on a lower peripheral surface and wherein the removably holding means comprises a hollow nipping member, the hollow nipping member having at least one set of depressions on an inner surface of the hollow nipping member, the protrusions on the push member lockably engaging with the at least one set of depressions on the hollow nipping member resulting in the lens being held in the non-deformed state.

22. The intraocular lens insertion system of claim 21, wherein the hollow nipping member further has a second set of depressions on a lower portion of the inner surface of the hollow nipping member than is the first set of depressions, the protrusions of the push member lockable engaging with the second set of depressions of the hollow nipping member resulting in the lens being held in the deformed position.

23. An insertion system for a deformable intraocular lens, the system comprising:

[packaging] *a package* for [removably holding the deformable intraocular lens] *storing the lens in a state in which no stress acts on the optical portion of the lens*;

an insertion device having a major axis, the insertion device defining a tubular portion and having a means for removably holding the package, the means for removably holding being associated with and in communication with the tubular portion, the means for removably holding defining a support which lies parallel to the major axis and an open portion opposite the support, the open portion shaped to receive the package; and a pushing mechanism for movement within the tubular portion and the means for removably holding, the pushing mechanism acting to deform the lens and push the lens without the package out of the insertion system.

24. The insertion system of claim 23 wherein the means for removably holding has a means for connecting to the package and receives the deformable intraocular lens in a non-deformed position.

25. The insertions system of claim 23 wherein the package defines an opening for release of the deformable intraocular lens.

26. The insertion system of claim 23 wherein the means for removably holding has two sides connected to the support, the two sides being situated opposite of each other and each having a major surface, one of the two sides having its major surface abutting and communicating with the tubular portion.

27. The insertion system of claim 23 wherein the deformable intraocular lens has an optical portion and support portions connected to the optical portion, the package having an inner surface and an outer surface, wherein the package interacts with the support portions so that the optical portion remains free from contact with the inner surface of the package.

28. The insertion system of claim 23 wherein the package is a quadrilateral shape.

29. A method for intraocular lens insertion by means of an insertion device having a removable holding means and a lens moving device, the method comprising the steps of:

placing a deformable lens in the removable holding means;

lockably engaging the lens moving device with the removable holding means in a first position, whereby the removable holding means holds the deformable lens in a non-deformed state;

lockably connecting the lens moving device with the removable holding means in a second position, whereby the removable holding means holds the deformable lens in a deformed state; and pushing the deformable lens through the insertion device into an eye.

30. The method for intraocular lens insertion of claim 29 whereby in the step of lockably engaging a center of the lens does not coincide with a center axis of a pushing mechanism and in the step of lockably connecting the center of the lens coincides with the center axis of the pushing mechanism.

31. The method as claimed in claim 29 wherein the step of lockably engaging further comprises the step of supporting the lens whereby an optical portion of the lens remains free from contact with an inner surface of the removable holding means.

* * * * *